United States Patent [19]

Ratliff et al.

[11] Patent Number: 5,618,916
[45] Date of Patent: Apr. 8, 1997

[54] PURIFIED PROTEIN WHICH FUNCTIONS AS A MYCOBACTERIAL RECEPTOR FOR FIBRONECTIN

[75] Inventors: Timothy J. Ratliff; Eric J. Brown, both of St. Louis, Mo.

[73] Assignee: The Jewish Hospital of St. Louis, St. Louis, Mo.

[21] Appl. No.: 265,450

[22] Filed: Jun. 24, 1994

Related U.S. Application Data

[63] Continuation of Ser. No. 1,028, Jan. 6, 1993, abandoned.
[51] Int. Cl.⁶ .......................... C07K 1/00; A61K 39/395
[52] U.S. Cl. .......................... 530/350; 530/355; 530/382; 530/388.1; 530/388.4; 530/388.85; 530/825; 424/130.1; 424/143.1; 424/164.1; 424/168.1; 424/248.1
[58] Field of Search .................... 530/350, 355, 530/382, 388.1, 388.4, 388.85, 825; 424/85.81, 85.91, 92, 93 K, 130.1, 143.1, 164.1, 168.1, 248.1; 436/829

[56] References Cited

U.S. PATENT DOCUMENTS 5,194,257  3/1993  Ratliff et al. .......................... 424/93 K

OTHER PUBLICATIONS

Abou–Zeid et al, *Infection and Immunity*, vol. 56, No. 12, pp. 3046–3051, Dec. 1988.
Aslanzadeh et al, *Chemical Abstracts*, vol. 112, p. 444, Ref. #4445c, 1990 (J. Gen. Microbiol. 1989, 135 (10), 2735–41).
Ratliff et al, *J. Gen. Microbiol.*, vol. 134, pp. 1307–1313, 1988.
Hudson et al, *Chemical Abstracts*, vol. 115, p. 32, Ref. #8496:a, 1991 (Cancer Res. 1991, 51(14) 3726–32).
Valentin. Weigand et al, *Chemical Abstracts*, vol. 116, p. 444, Ref. #231763f, 1992 (Res. Microbiol. 1992, 143 (1), 75–9).
Godfrey et al, *Infection and Immunity*, vol. 60, No. 6, pp. 2522–2528, Jun. 1992.
Rao et al, *Infection and Immunity*, vol. 60, No. 9, pp. 3652–3657, Sep. 1992.

*Primary Examiner*—Christina Y. Chan
*Assistant Examiner*—Abdel A-Mohamed
*Attorney, Agent, or Firm*—Senniger, Powers, Leavitt & Roadel

[57] ABSTRACT

A method for the treatment of superficial urinary tract tumors in a mammal involves administering a diagnostically effective amount of a liposomal composition comprising a liposome, a chemotherapeutic agent or immune activating drug carried by the liposome and a purified protein which functions as a mycobacterial receptor for fibronectin on the surface of the liposome whereby the liposomal composition becomes attached to and internalized in the cells of the tumors. In lieu of the purified protein an antibody to an integrin receptor on the surface of the cells of the tumors may be used or a delivery system composed of a conjugate of a chemotherapeutic agent or immune activating drug and an antibody to an integrin receptor may be employed.

1 Claim, 12 Drawing Sheets
(1 of 12 Drawing(s) in Color)

PURIFIED PROTEIN WHICH FUNCTIONS AS A MYCOBACTERIAL RECEPTOR FOR FIBRONECTIN

This is a continuation, of application Ser. No. 08/001,028, filed Jan. 6, 1993, now abandoned.

BACKGROUND OF THE INVENTION

This invention relates to a purified protein which functions as a mycobacterial receptor for fibronectin and to improved methods for the treatment of superficial urinary tract tumors.

The efficacy of adjuvant intravesical Bacillus Calmette-Guerin (BCG) for superficial bladder cancer was first reported by Morales and associates in 1976. Morales et al., J. Urol. 116: 180–183, 1976. Although the efficacy of BCG is clearly established, the mechanisms by which BCG mediates antitumor activity are not clearly understood.

Previous studies have shown that BCG attachment to fibronectin (FN) in the bladder lumen is required for the development of an antitumor response. Kavoussi et al., J. Clin. Invest. 85: 62–67, 1990. Inhibition of FN-mediated BCG attachment was shown in these studies to inhibit immunization, the expression of delayed type hypersensitivity and antitumor activity. Further studies showed that BCG-mediated antitumor activity was dependent on T lymphocytes. Ratliff et al., J. Urol. 137: 155–158, 1986. These studies led to the hypothesis that BCG-induced antitumor activity is comprised of a series of event which begin with attachment and progress through immune activation and culminate in tumor destruction.

Recent studies demonstrated that BCG attach to and are ingested by bladder epithelial cells. Becich et al., J. Urol. 145: 1316–1324, 1991. Although the role of cellular attachment and ingestion by epithelial cells in BCG-mediated antitumor activity has not been clearly established, this observation suggests that BCG interaction with tumor cells may be associated with immune modulation. There remains a need to more clearly define the interaction of transitional epithelial carcinoma cells with BCG.

In addition, in vitro characterization studies have demonstrated that BCG, as well as other mycobacteria tested, attached to FN-coated surfaces but not surfaces coated with laminin, fibrinogen, or Type IV collagen. Ratliff et al., Cancer Res. 47: 1762–1766, 1987 and Ratliff et al., J. Gen. Microbiol. 134: 1307–1313, 1988. The BCG/FN interaction was saturable, FN specific, essentially irreversible and inhibited by pretreatment with protease suggesting the presence of specific bacterial receptor. Aslanzadeh et al., J. Gen. Microbiol. 135: 2735–2741, 1989. Further studies showed that BCG attachment to FN was inhibited by components contained in the supernatants of proliferating BCG suggesting that the receptor(s) were released into the supernatant. Abou-Zeid et al., Infect. and Immun., 56: 3046–3051, 1988 and Ratliff et al., J. Gen. Microbiol, 134: 1307–1313, 1988. This hypothesis was supported by several independent observations including: (a) radiolabelled proteins from BCG supernatants attached to FN-coated surfaces, Abou-Zeid et al., supra; (b) the supernatant component(s) inhibited the attachment of BCG to FN, Ratliff et al., J. Gan. Microbiol., supra; (c) the inhibitory activity was removed from affinity chromatograph on FN-Sepharose, Ratliff et al., J. Gen. Microbiol., supra; and (d) proteins from BCG supernatants separated on sodium dodecyl sulfate-polyacrylamide gel electrophoresis (SDS-PAGE) and blotted to nitrocellulose bound FN, Abou-Zeid et al, supra.

There has been a need to characterize and evaluate the components involved in BCG attachment and ingestion or internalization by the bladder tumor cell line and to develop improved delivery systems for the treatment of superficial urinary tract tumors.

SUMMARY OF THE INVENTION

Among the several objects of the invention may be noted the provision of improved methods for the treatment of superficial urinary tract tumors; the provision of such methods which involve the use of delivery systems which promote the attachment to and internalization in the cells of such tumors of chemotherapeutic agents or immune activating drugs; and the provision of a novel purified protein which functions as a mycobacterial receptor for fibronectin and which may be utilized in methods for the treatment of superficial urinary tract tumors. Other objects will be in part apparent and in part pointed out hereinafter.

Briefly, the present invention is directed to a method for the treatment of superficial urinary tract tumors in a mammal which comprises administering to the mammal a diagnostically effective amount of a liposomal composition comprising a liposome, a chemotherapeutic agent or immune activating drug carried by the liposome and the purified protein of the invention on the surface of the liposome whereby the liposomal composition becomes attached to and internalized in the cells of the tumors. In lieu of such liposomal composition, other delivery systems may be employed in accordance with the invention such as a liposomal composition comprising a liposome, a chemotherapeutic agent or immune activating drug carried by the liposome and an antibody to an integrin receptor on the surface of the liposome, the antibody being an antibody to an integrin receptor on the surface of the cells of the tumors, or a delivery system composed of a conjugate of such an agent or drug and such an antibody to an integrin receptor. The invention is also directed to a purified protein which functions as a mycobacterial receptor for fibronectin.

BRIEF DESCRIPTION OF THE DRAWINGS

"The file of this patent contains at least one drawing executed in color. Copies of this patent with color drawing(s) will be provided by the Patent and Trademark Office upon request and payment of the necessary fee."

FIGS. 2A–2C show the results of SDS-PAGE of fractions obtained during the purification of the mycobacterial FN receptor as follows;

FIG. 8A–8C show discrimination between attachment and ingestion using the dual fluorescence assay.

FIG. 9A 23,000; FIG. 9B 90,000; FIG. 9C 59,000;

FIGS. 10A–10B are graphs showing the effect of anti-integrin antibodies on the attachment and ingestion of SCG by T-24 cells. FIG. 10A: attachment; FIG. 10B: ingestion. The antibody concentrations were 1:10 dilutions of the preparations and were determined to provide maximal inhibitory activity;

DESCRIPTION OF THE PREFERRED EMBODIMENTS

In accordance with the present invention, it has now been found that a purified protein which functions as a mycobacterial receptor for fibronectin (FN) may be isolated from concentrated supernatants of *Mycobacterium vaccae*, *Mycobacterium boris bacillus* Calmette-Guerin (BCG) or other sources. This purified protein is characterized by:

(a) binding directly to fibronectin, said binding being inactivated by trypsin;

(b) being essential for attachment of bacillus Calmette-Guerin to fibronectin;

(c) binding directly to fibronectin-coated surfaces;

(d) having a primary protein band at 55 kDa as determined by sodium dodecyl sulfate-polyacrylamide gel electrophoresis analysis on pooled fractions containing said purified protein;

(e) inhibiting fibronectin attachment to bacillus Calmette-Guerin in a dose-dependent manner;

(f) having a monoclonal antibody thereto block the attachment of bacillus Calmette-Guerin to fibronectin-coated surfaces; and (g) having a polyclonal antibody that recognizes only the 55 kDa band in unfractionated bacterial extracts.

In further accordance with the invention, it has been found that improved delivery systems for delivering chemotherapeutic agents or immune activating drugs for attachment to and internalization in the cells of superficial urinary tract tumors reside in certain liposomal compositions or conjugates which can be administered to mammals in diagnostically effective amounts for the treatment of such urinary tract tumors. One such delivery system resides in a liposomal composition comprising a liposome, a chemotherapeutic agent or immune activating drug carried by the liposome and the above-noted purified protein of the invention on the surface of the liposome. Another delivery system resides in a liposomal composition comprising a liposome, a chemotherapeutic agent or immune activating drug carried by the liposome and an antibody to an integrin receptor on the surface of the liposome, the antibody being an antibody to an integrin receptor on the surface of the cells of urinary tract tumors. Still another delivery system resides in a conjugate of a chemotherapeutic agent or immune activating drug and an antibody to an integrin receptor on the surface of the cells of the tumors. With each of these delivery systems, the administration of diagnostically effective amounts advantageously results in the liposomal composition or conjugate becoming attached to and internalized in the cells of urinary tract tumors to thereby eliminate such cells.

Among the chemotherapeutic agents or immune activating drugs which may be used in the practice of the invention may be mentioned Thiotepa, Adriamycin (doxorubicin), mitomycin C, heat killed bacillus Calmette-Guerin (BCG) or BCG subfractions, interleukins 1–10, alpha, beta and gamma interferons and alpha and beta tumor necrosis factors.

Liposomes for use in preparing the above-mentioned liposomal compositions are known in the art and generally comprise lipid materials including lecithin and sterols, egg phosphatidyl choline egg phosphatidic acid cholesterol and alpha-tocopherol. Useful liposomes may be prepared as generally described in Kimelberg et al., CRC Grit. Rev. Toxicol. 6, 25 (1978) and Yatvin et al., Medical Physics, Vol. 9, No. 2, 149 (1982).

As shown by the experimental data presented hereinafter, a purified protein (referred to herein as p55) which functions as a mycobacterial receptor for fibronectin has been isolated from the supernatant of *M. vaccae* or BCG and has demonstrated its ability to bind directly to FN-coated surfaces. This inhibitory component in the supernatant of *M. vaccae* or BCG presumably inhibited BCG attachment to FN by competing for FN binding sites, a result consistent with previous observations, Ratliff et al., J. Gen. Microbiol., supra.

The data presented hereinafter are consistent with the hypothesis that p55 is a mycobacterial receptor for FN. Purified p55 was observed both to inhibit the binding of FN to BCG and to bind directly to FN-coated surfaces. In addition, p55 localizes to the particulate fraction of the bacterium suggesting its availability for binding. Most convincingly, monoclonal antibody to p55 blocked the attachment of viable BCG to FN-coated surfaces. Importantly, although p55 was purified from *M. vaccae*, both the monoclonal and polyclonal antibodies recognize BCG. The mFNR.1 monoclonal anti-p55 also inhibits the binding of *M. avium*, *M. tuberculosis* and *M. kansasii* to FN-coated surfaces. These data suggest that the 55 kda protein is a highly conserved protein or a member of an antigenically related family of proteins that function as mycobacterial FN receptors.

The data presented hereinafter also demonstrate that p55 binds to FN and is necessary for BCG attachment to FN. They do not rule out the involvement of additional components in FN binding. Since FN is known to interact with glycolipids, which are abundant in the mycobacterial envelope, there may be as yet unidentified components involved in binding.

The binding of BCG to FN is a necessary step in the development of an anti-tumor response after the intravesical instillation of BCG for bladder cancer. Kavoussi et el., J. Clin. Invest. 85: 62–67, 1990. Our studies have demonstrated that only when BCG attached to FN was it retained with an avidity sufficient to induce an antitumor response. In vitro and in vivo studies showed that BCG were ingested by bladder tumor cells leading to the hypothesis that internalization was a secondary step that occurred after BCG attachment to FN. Becich et al., J. Urol. 145: 1316–1324, 1991. In accordance with the present invention, we have discovered an additional, unexpected role for FN. In addition to its role in retention of the BCG in the bladder, FN acts as a critical signal for binding and internalization of BCG by the epithelial tumor cells.

The role of FN in attachment and ingestion appears to be opsonic. This hypothesis is supported by data from several experiments. First, the preopsonization of BCG by FN markedly enhances both attachment and ingestion. Not only was the percentage of cells ingesting BCG increased, but there also was a marked increase in the number of bacteria ingested by each cell. Furthermore, FN-coated latex beads but not LN-coated beads competed with BCG for attachment and ingestion sites. Finally, a monoclonal antibody to a BCG FN binding protein blocked both attachment and ingestion. While an opsonic role for FN has been reported for other bacterial species, opsonization in these reports resulted in attachment but did not initiate ingestion or internalization. Hamill et al. Infec. & Immun. 54: 833–836, 1986 and Van de Water et al., Science 220: 201–204, 1983. In our studies, FN opsonization of BCG also initiated ingestion.

An alternative hypothesis is FN induced modulation of a distinct receptor. Previous studies demonstrated that FN upregulates complement and Fc receptors (Bohnsack et al., J. Urol. 135: 2680–2686, 1984 and Bevilacqua et al., J. Exp. Med. 153: 42–60, 1981); however, these receptors are not expressed on T-24 cells. The modulation of unknown phagocytic receptors for BCG cannot be definitively excluded, although our data are supportive of a direct opsonic role for FN.

Previous studies have evaluated the effect of FN on bacterial attachment and phagocytosis by macrophages, neutrophils and endothelial cells. These studies have uniformly shown FN to mediate attachment but not to initiate ingestion. Van de Water et al (supra) showed that the phagocytosis of *Staphylococcus aureus* and *Salmonella typhimurium* by several phagocytic cell types was independent of FN. These observations were supported by Proctor and associates (Blood, 59: 681–687, 1982) who showed FN-mediated attachment but not ingestion of *S. aureus* by human neutrophils. Hamill et al. (supra) investigated the effects of FN on *S. aureus* ingestion by cultured bovine aortic endothelial cells. These investigators observed an FN-induced increase in the attachment of *S. aureus* to the endothelial cells, but FN had no effect on phagocytosis.

In a review of bacterial attachment mechanisms, Isberg (Cell, 60: 861–871, 1990) suggested that the primary function of bacterial attachment to extracellular matrix proteins was colonization, while the initiation of ingestion required attachment of bacteria to integrin receptors. This hypothesis was supported by studies on Yersinia pseudotuberculosis invasion of mammalian epithelial cell lines. Leininger et al. Proc. Natl. Acad. Sci., USA 88: 345–349, 1991. In these studies the protein invasin, which is known to be sufficient for inducing attachment and ingestion by traditionally nonphagocytic cells, was shown to attach to $\beta_1$ integrin receptors. Similar results were reported for Bordetella pertussis. Our results also demonstrate bacterial attachment to an epithelial cell $\beta_1$ integrin receptor, the $\alpha_5\beta_1$ FN receptor; however, the attachment mechanism differs from those previously reported for other bacteria, since FN opsonization of BCG is required. In addition BCG attachment via the FN bridge initiated ingestion by this epithelial cell line.

The attachment and ingestion of mycobacteria to traditionally nonphagocytic cells is well established. The phenomenon is best characterized for *M. leprae* in which phagocytosis has been documented for muscle cells, neurons, endothelial cells, fibroblasts and Schwann cells (Band et al., Int. J. Lepr. 54: 294–299, 1987; Cornette et al., Int. Archs. Allergy Appl. Immun., 86: 139–146, 1988; and Griffin et al., J. Exp. Med., 142: 1263–1282, 1975). While ingestion is best characterized for *M. leprae*, it has been observed for *M. tuberculosis*, BCG, *M. fortuitum*, *M. ulcerans* and *M. balnei* (Shepard, J. Exp. Med. 105: 237–245, 1957) The in vivo importance of this phenomenon is not clear but previous investigators suggested that Schwann cells may be a primary and persistent source of *M. leprae* (Stoner, Lancet, 1: 994–996, 1979) Several other mycobacterial species attach to epithelial cells and are ingested via $\beta_1$ integrin receptors as is described for BCG; all require FN opsonization. These data suggest that mycobacterial uptake into epithelial cells via FN opsonization is a uniform phenomenon for this bacterial genus. Preliminary data suggest that this mechanism also is operative in macrophages, the more traditional residence of invasive mycobacteria. These data also suggest that a re-examination of the role of ephithelial cell invasion in mycobacterial pathogenesis is in order. While little attention has been focused on this aspect of infection, it is clear that mycobacterial invading through the gut or the respiratory tract need to cross an epithelial border before systemic invasion is possible.

The mechanism(s) by which BCG mediates antitumor activity have not been defined. Based on our current and past studies, we hypothesize that FN attachment to the mycobacterial FN receptor plays a key role in this process. Not only does this receptor mediate retention of BCG at tumor sites (Kavoussi et al., supra), but it also plays a critical role in uptake by the epithelial tumors themselves. Presumably, uptake is followed by lysosomal degradation and antigen presentation to the immune system.

The following examples illustrate the practice of the invention.

EXAMPLE 1

Chemicals. All chemicals were purchased from Sigma (St. Louis, Mo.) and were reagent grade unless otherwise stated.

Bacteria. BCG were obtained from Armand Frappier, Quebec, Canada, as a lyophilized preparation containing $10^7$ colony forming units (CFU) $mg^{-1}$ (manufacturer's specification). Before use, BCG was cultured in Youman's medium for 5 d at 37° C. The bacteria were harvested by centrifugation and resuspended in buffer to produce approximately $7\times10^8$ CFU ml$^{-1}$ (determined by standard curves plotting OD$_{570}$ vs CFU). *M. vaccae* was obtained from the mycobacterial culture collection of Dr. John Stanford, University of London, London, England. *M. vaccae* was grown in Sauton medium and stored at $-70°$ C. as described. Sher et al., Infect and Immun., 8: 736–742, 1973.

Preparation of $^{125}$I-labelled FN. Human plasma FN was purified as previously described (Kavoussi et al., supra.). The purified FN, 1.5 mg ml$^{-1}$ was labelled for 15 minutes with 1 mCi (37 MBq) $^{125}$INa (Amersham) in a test-tube precoated with 200 μg Iodo-Gen (1,3,4,6-tetrachloro-3,6-diphenylglycouril) as previously described. Aslanzadeh et al., supra. The labelled FN was then separated from unbound $^{125}$I by chromatography on a 10 ml Sephadex G25 column. The specific activities of the labelled FN preparations were routinely between $10^6$ and $10^7$ cpm μg$^{-1}$.

$^{125}$I-FN Binding assay. The binding assay was performed as previously described. Aslanzadeh et al., supra. Briefly, six micrograms of $^{125}$I-FN was added to 1.5 ml volume microcentrifuge tubes (Eppendorf) precoated for 2 h with 1 ml of 1 mg ml$^{-1}$ human serum albumin (HSA). Prior to $^{125}$I-FN addition, $7\times10^6$ BCG suspended in 1.0 ml of 0.1M-Tris buffer, pH 6.0, was added. The $^{125}$I-FN was mixed with either 300 μl unlabelled FN (1 mg ml$^{-1}$) or 300 μl of TRIS only to determine non-specific and total binding, respectively. Specific binding was ascertained by subtracting nonspecific from total binding. The reaction mixtures were incubated for 1 h at 22° C. After incubation, the microcentrifuge tubes containing the reaction mixtures were centrifuged at 10,000 g for 3 min in a Beckman Microcentrifuge B. The supernatant, containing free radiolabelled FN, was carefully removed. The microcentrifuge tubes were sliced and the pellets containing the radiolabelled FN bound to BCG were analyzed for radioactivity. Control experiments using $^{125}$I-FN without bacteria produced background counts of approximately 500 cpm.

Attachment of BCG to FN-coated surfaces. The matrix attachment assay was performed by a modification of a previously described method. Ratriff et al., J. Gen. Microbiol, supra. Briefly, a 5 day culture was washed twice with and resuspended in phosphate-buffered saline (PBS), pH 7.2, to a concentration of $10^8$ CFU/ml. $10^7$ CFU (0.1 ml) was added to each well of a 96 well microtiter plate (Immulon II, Dynatech Laboratories, Inc., Chantilly, Va.) previously coated with (120 μg/ml) of FN or HSA (120 μg/ml; background). Attachment was quantitated by reading the optical density at 570 nm on an ELISA reader. The results are reported as OD units.

Production of Receptor-Containing Supernatants. *M. vaccae* were subcultured in 100 ml of Sautons medium to plateau growth phase. An innoculum of $8\times10^8$ bacteria were cultured in each of eight flasks containing 1.0 L of Sautons. Cultures were maintained at 37° C. in 7% $CO_2$ for 3 weeks. Supernatants were harvested by centrifugation and residual bacteria were removed by filtration (2 micron filters, Costar). The supernatant was concentrated 100 times on an Amicon filtration unit with a PM 10 filter. Concentrated *M. vaccae* culture supernatant was dialyzed against distilled $H_2O$ and lyophilized.

Purification of the FN-Binding Protein. Concentrated *M. vaccae* culture supernatant was dialyzed against distilled $H_2O$ and lyophilized. The lyophilized supernatant was reconstituted to 1.5 ml with 0.02M Bis-Tris, pH 6.0, and 0.7 ml was loaded onto an ACA 54 gel filtration column (0.6 cm×75 cm) equilibrated with 0.02M Bis-Tris.

Inhibitory fractions were pooled and loaded onto 10 ml of DEAE-Sephacel. The column was washed with 0.02M Bis-Tris, pH 6.0 until the effluent was protein free. Protein was eluted with a 0–0.4M NaCl gradient in Bis-Tris. Fractions, 1.0 ml, were collected and dialyzed against Bis-Tris, pH 6.0. SDS-PAGE and Western blots were performed as described. Abou-Zeid et al., supra.

Antibodies. Polyclonal rabbit antibodies to the purified adhesin (p55) was prepared by injecting subcutaneously 25 μg in alum. At 3 week intervals the rabbis was boosted with 15–20 μg in alum. Ten to 14 days after the second boost antibody was harvested. IgG was isolated from serum by 50% ammonium sulfate precipitation followed by DEAE-Sephacel ion exchange chromatography. SDS-PAGE demonstrated only bands consistent with IgG heavy and light chains. All experiments using the polyclonal antibody were performed with DEAE purified antibody.

Monoclonal antibody to the p55 protein was generated by the subcutaneous injection of BALB/C mice with 10 μg p55 in alum. Mice were boosted three times at weekly intervals with 5 μg p55 in alum. Mice were rested 3–4 weeks after the third boost and injected IV with 5 μg p55 in PBS. Three days later spleens were harvested and fused with the NS1 myeloma. Reactive clones were detected by ELISA with purified p55-coated microtiter wells. A single hybridoma showed consistent reactivity in an ELISA assay. The reactive hybridoma was clones, and the antibody, designated mFNR.1, isotyped as IgMλ.

p55 FN binding Assay. Immulon wells were coated with FN or BSA as a control for non-specific binding, as described above. The remaining attachment sites were blocked by the addition of 1% bovine serum albumin (BSA) in PBS for 30 min. Purified p55 in Tris buffer was added to appropriate wells (3 μg/well) and incubated for 30 min at room temperature. Wells were washed and purified mFNR.1 diluted in PBS containing 0.1% BSA was added for 1 hr. at room temperature. The wells were washed and a biotinylated anti-mouse IJ (Sigma Chemicals, St. Louis, Mo.) was added at a predetermined optimal concentration for 1 hr. at room temperature. The wells were washed, and the reaction was developed by the addition of p-Nitrophenyl phosphate. Reactivity was read on an ELISA reader at a wave length of 405 nm. Controls included p55 added BSA-coated wells, FN-coated wells without p55, and FN-coated wells with a nonspecific primary isotype control (RL172.4; anti-thy 1.2). Control absorbance for all controls was equal to or less than that of the isotype control.

Results

Figure 1:
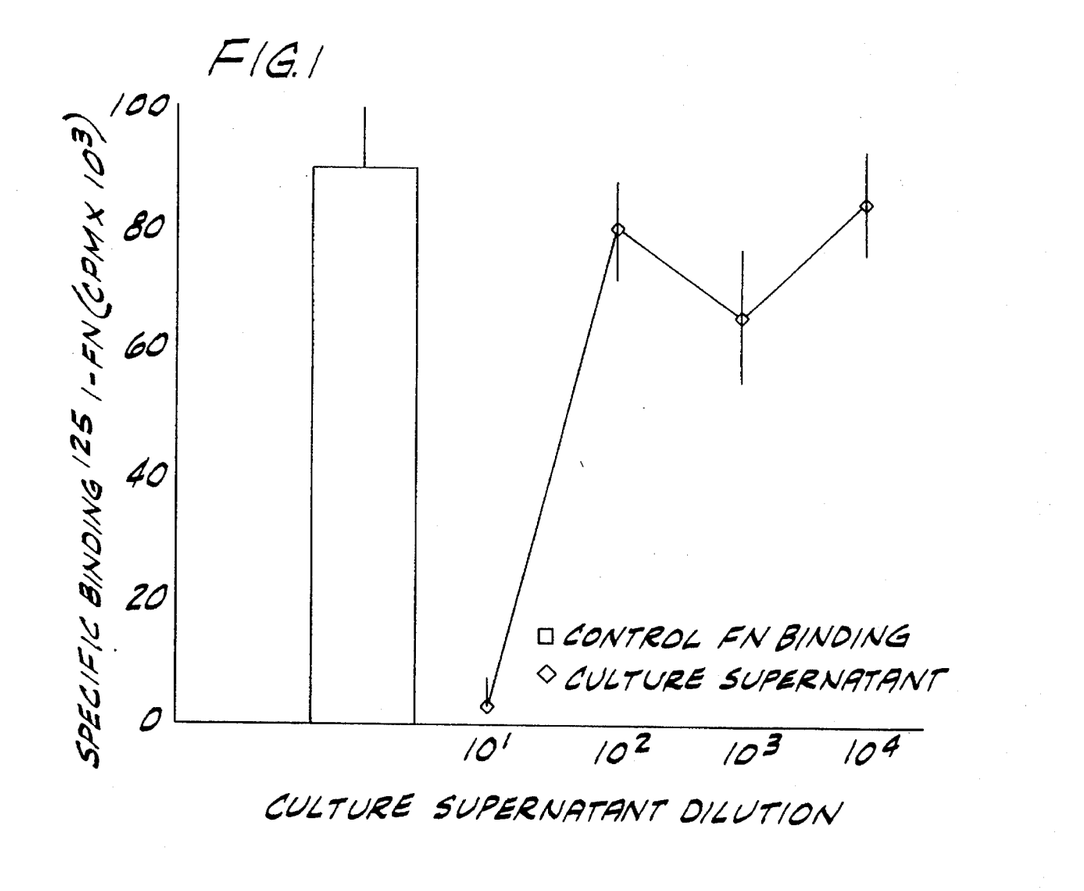
FIG. 1 is a graph showing the effect of M. vaccae culture supernatant on $^{125}$I-FN binding to BCG.
Figure 2A:
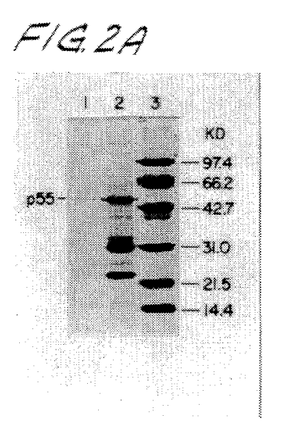
FIG. 2A lane 1—pooled inhibitory fractions from ACA-54 gel filtration column; lane 2—concentrated unfractionated M. vaccae supernatant; lane 3—MW standards.
Figure 2B:
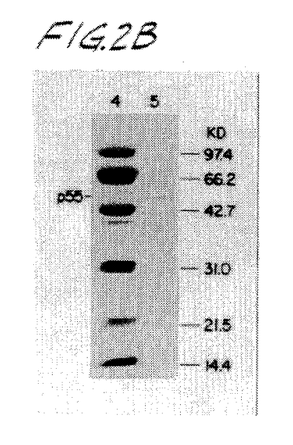
FIG. 2B: lane 4—MW standards; lane 5—DEAE-Sephacel inhibitory fraction.

Concentrated *M. vaccae* supernatant contains a component that inhibits FN binding to BCG (FIG. 1). Purification of the inhibitory component(s) was initiated by applying supernatant to an ACA-54 gel filtration column previously equilibrated with Bis-Tris, pH 6.0. The inhibitory activity was localized and pooled for further purification. SDS-PAGE on the pooled fractions revealed a primary protein band at 55 kDa (p55; FIG. 2A, lane 1). The pooled ACA-54 inhibitory fractions were applied to a DEAE-Sephacel anion exchange column equilibrated with 0.02M Bis-Tris, pH 6.0. Bound protein was eluted with a 0–0.4M NaCl gradient in Bis-Tris, pH 6.0. The peak inhibitory activity eluted at 0.3M NaCl. SDA-PAGE on the 0.3M fraction revealed a single 55 kDa protein band (FIG. 2B, lane 5). The protein from this fraction was used for all subsequent experiments and for immunization purposes. The protein purification scheme is summarized in Table 1. Amino acid sequencing by Edman degradation was unsuccessful, presumably because the amino terminus of p55 was blocked.

TABLE 1

Purification of p55

| STEP | PROTEIN (mg/ml) | VOLUME | TOTAL PROTEIN | FOLD PURIFICATION |
| --- | --- | --- | --- | --- |
| Conc. Supernatant | 11.16 | 0.7 | 7.8 | — |
| ACA 54 Gel Filtration | 0.07 | 8.0 | 0.57 | 13.7 |
| DEAE-Sephacel (0–0.4 NaCl) | 0.16 | 2.0 | 0.32 | 24.3 |

Figure 3:
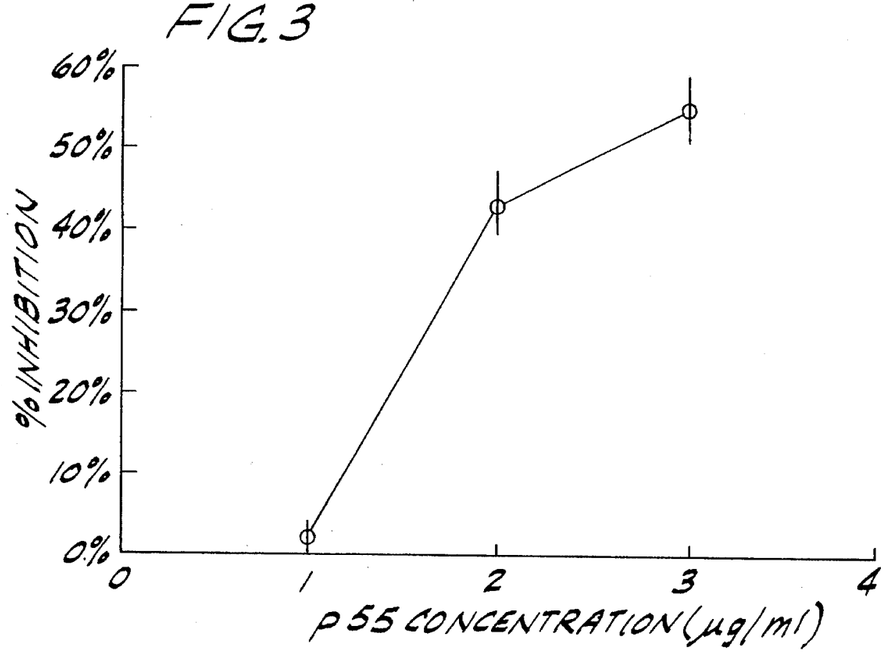
FIG. 3 is a graph showing inhibition of $^{125}$I-FN attachmnt to BCG by purified p55.

The purified p55 was tested for its ability to inhibit $^{125}$I-FN binding to BCG (FIG. 3). Purified p55 inhibited FN attachment to BCG in a dose-dependent manner.

Figure 2C:
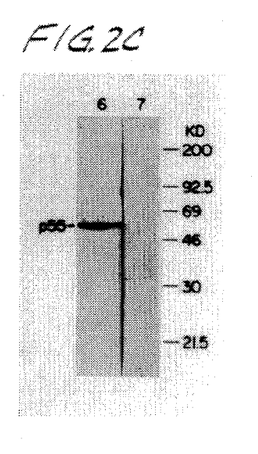
FIG. 2C: lane 6—Western blot of unfractionated M.vaccae supernatant using rabbit polyclonal anti-p55; lane 7—blot with preimmune serum.
Figure 4:
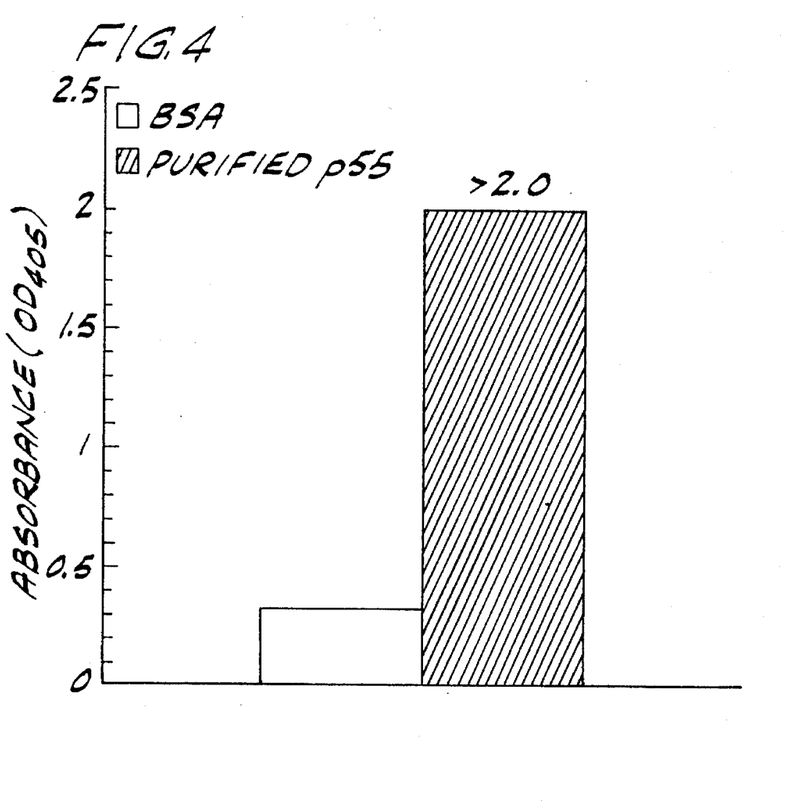
FIG. 4 is a graph showing recognition of purified M. vaccae p55 protein by monoclonal anti-p55 (mFNR.1)

Purified p55 was used as an immunogen to generate a rabbit polyclonal and a mouse monoclonal antibody. The resulting polyclonal antibody blotted a single protein band at 55 kDa in crude *M. vaccae* supernatants (FIG. 2C, lane 6). The single monoclonal antibody obtained was reactive by ELISA to purified p55 (FIG. 4) but was not effective in Western blots (data not shown).

Figure 5:
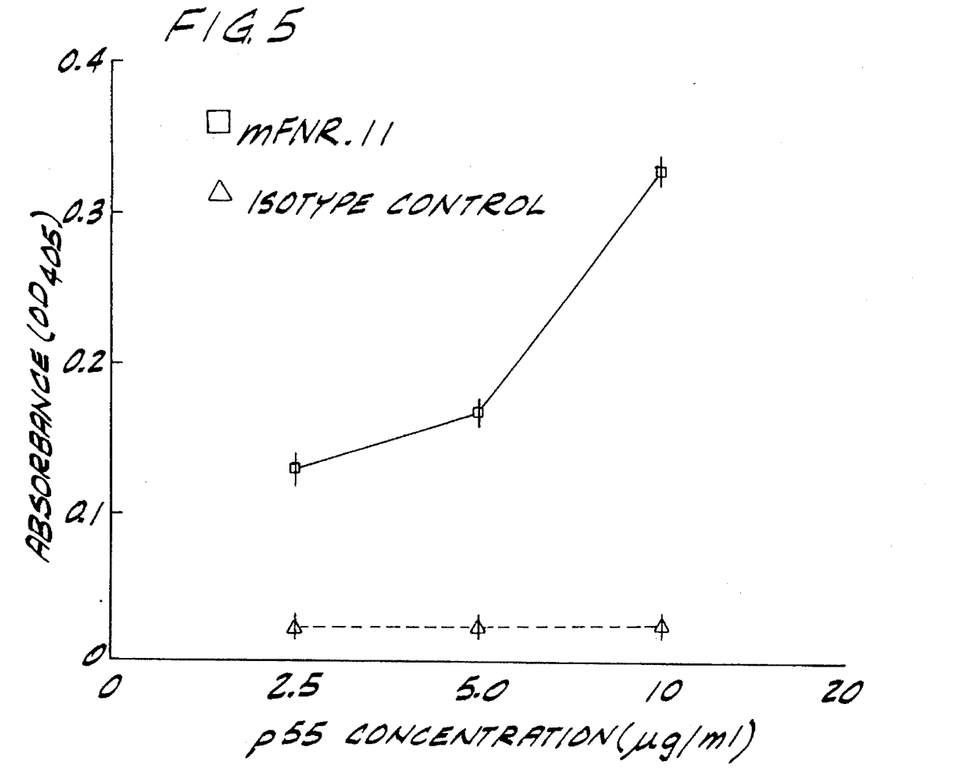
FIG. 5 is a graph showing attachment of purified p55 to FN-coated surfaces.

Further studies were performed to determine whether the purified p55 protein bound to FN. Microtiter wells were coated with FN as described above, after which purified p55 was added. The binding of p55 to FN was detected by either the polyclonal or monoclonal antibodies. The results were identical for both. Data for the monoclonal antibody (mFNR.1) are shown in FIG. 5. The results demonstrate mFNR.1 binding to p55 treated FN coated surfaces increases as a function of the input of p55 suggesting a p55/FN interaction. Thus, p55 inhibits FN binding to BCG and binds directly to FN. Taken together the data show that the purified inhibitory component (p55) from the supernatant of *M. vaccae* is a FN binding protein.

Figure 6:
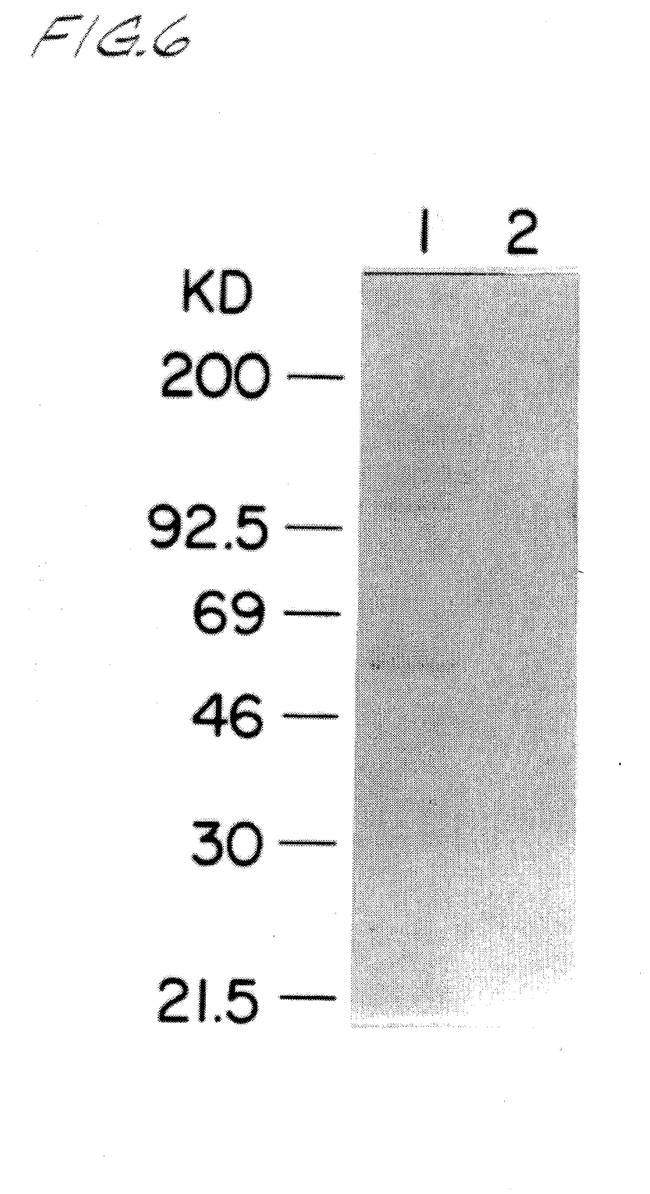
FIG. 6 is a Western blot of particulate and soluble BCG fractions using rabbit polyclonal anti-p55. BCG were sonicated and particulate and soluble fractions were separated by centrifugation.

Because this *M. vaccae* FN-binding protein had been purified based on its ability to inhibit FN binding to BCG, it was reasonable the BCG should contain a related protein. Therefore, we tested whether the polyclonal anti-p55 (made against *M. vaccae* FN-binding protein) recognized any BCG protein(s). To do this BCG were fractionated into cytosolic and cell wall components as described. Hunter et al., J. of Immunol. 142: 2864–2872, 1989. The crude cell fractions were then subjected to Western blotting with the polyclonal anti-p55 (FIG. 6). An immunologically crossreactive protein at 55 kD was seen in the cell wall but not the cytosolic fraction from BCG. In addition, a protein at 100 kDa also faintly reacted with the antiserum. We are uncertain whether this represents an additional crossreactive protein in BCG or a precursor of the mature p55. Thus, BCG expresses a protein(s) crossreactive with the *M. vaccae* FN binding protein in the cell wall.

Figure 7:
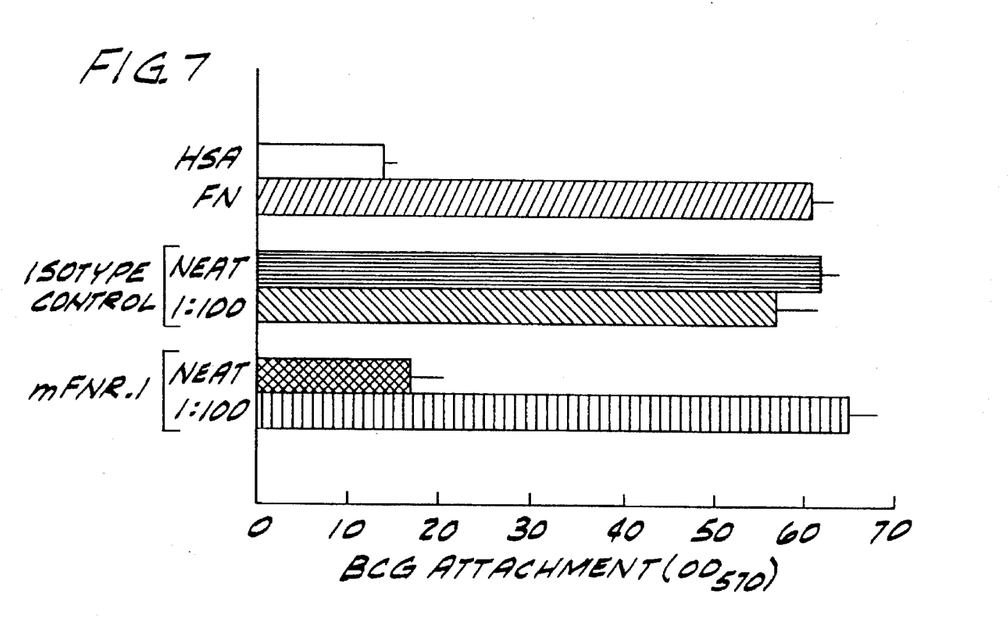
FIG. 7 is a graph showing inhibition of BCG attachment to FN-coated surfaces by mFNR.1.

Since the cell wall localization of p55 in BCG is consistent with its possible function as a FN receptor, we tested whether mFNR.1, the mAb anti-p55, could inhibit the binding of intact, viable BCG to FN. As shown in FIG. 7, mFNR.1 inhibits BCG binding to a FN-coated surface. Thus, an antigenically related protein is necessary for BCG binding to FN.

EXAMPLE 2

Bladder Tumor Cells. The human transitional cells carcinoma cell line, T-24 was obtained from American Type Culture Collection, Rockville, Md. The cells were cultured in medium containing Earle's minimum essential medium (MEM) supplemented with 50 units/ml penicillin, 50 units/ml streptomycin, 1% L-glutamine and 10% fetal calf serum. All tissue culture media and supplements were purchased from Washington University Cancer Center, St. Louis, Mo. Tests for mycoplasma were negative.

BCG. Pasteur strain (Armand Frappier, Quebec, Canada) at 120 mg/vial was used. The vaccine was a lyophilized preparation containing $10^7$ colony forming units (CFU) per milligram dry weight. A 120 mg ampule of BCG was suspended in 10 ml prewarmed RPMI-1640, and particles representing one or a few bacteria were isolated by a modification of the method reported by Rook and associates (Clin. Exp. Immunol. 59: 414–420, 1985).

The suspension was centrifuged at 3,000 g for 10 minutes at 24° C. After the medium was removed, BCG were resuspended in 10 ml RPMI-1640 and centrifuged at 250 g for 3 minutes at 24° C. to eliminate large clumps of bacteria. The top 5 ml of the suspension was removed and used in the attachment and ingestion assay. The number of organisms was determined by measuring the optical density at wave length of 570 nm, and comparing it to a previously established standard curve quantitating CFU from optical densities using the particle isolation technique described above.

Antibodies. Rabbit polyclonal anti-BCG and anti-FN antibodies were purchased from DAKO, Corp., Santa Barbara, Calif. Rat monoclonal antibodies, B1E5 directed against the $\alpha_5$ integrin subunit and AIIB2 directed against the $\beta_1$ integrin subunit were provided by Dr. Caroline Damsky, San Francisco, Calif. Hall et al. J. Cell Biol., 110: 2175–2184, 1990. Murine monoclonal antibody J143 directed against the $\alpha_3$ subunit was a gift from Dr. Lloyd J. Old, New York, N.Y., Fradet et al., Cancer Res., 46: 5183–5188, 1986. Rat monoclonal antibody 43909B directed against the $\beta_4$ subunit was a gift from Dr. Stephen Kennel, Oak Ridge, Tenn., Kennel et al., J. Biol. Chem. 264: 15515–15521, 1989. Monoclonal anti-vitro-nectin antibody was a gift from Dr. David Barnes, Corvallis, Oreg., Basara et al., Cancer Res. 45: 2487–2494, 1985. Fluorescein isothiocyanate (FITC) conjugated goat F(ab')$_2$ anti-rabbit IgG and rhodamine isothiocyanate (RITC) conjugated goat F(ab')2 anti-rabbit IgG were obtained from Cappell, West Chester, Pa.

Extracellular Matrix Proteins. Human plasma FN was purified as previously reported, Pommer et al., J. Exp. Med. 157: 1844–1854, 1983. Murine LN was obtained from Collaborative Research, Bedford, Mass. Human vitronectin (VN) was purchased from Telios Pharmaceuticals.

Coating Latex Beads with Proteins. Latex beads were coated with proteins by absorption as described by Cantarero et al (Analytical Biochemistry 105: 375–382, 1980). Briefly, beads were washed in 0.1 phosphate buffered saline, pH 7.0 to remove surfactants. Washed beads were resuspended in PBS containing 200 μg/ml of the desired protein and incubated at room temperature overnight. The beads were washed and resuspended in RPMI-1640 supplemented with 0.1% BSA and 0.05% sodium azide. Stock preparations were stored at 4° C. Prior to use in an ingestions assay, the beads were washed, quantitated on a Coulter Counter and diluted in RPMI-1640.

BCG Ingestion Assay. T-24 cells were removed from tissue culture flasks using 10 mM ethylenediaminetetracetic acid (EDTA) in phosphate buffered saline (PBS; pH 7.2). $10^5$ cells in Earle's MEM with the same supplements described above were plated into each well of Lab-Tek 8 chamber slides (Miles Laboratories, Naperyilia, Ill.). The cultures were incubated at 37° C. in 5% $CO_2$ overnight. Alternatively, T-24 cells were plated in Lab-Tek chambers precoated overnight with FN, LN or VN as previously described. Coplen et al., J. Urol., 145: 1312–1315, 1991.

Cells were allowed to attach for 2 hours. Attached cells were washed twice with prewarmed PBS, and $10^5$ CFU BCG were added into each chamber containing adherent T-24 cells. The cultures were incubated at 37° C. in 5% $CO_2$ for 3 hours to allow BCG internalization.

Figure 8A:
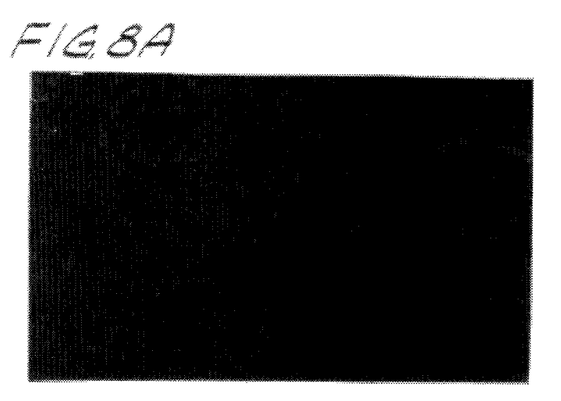
FIGS. 8A phase contrast.
Figure 8B:
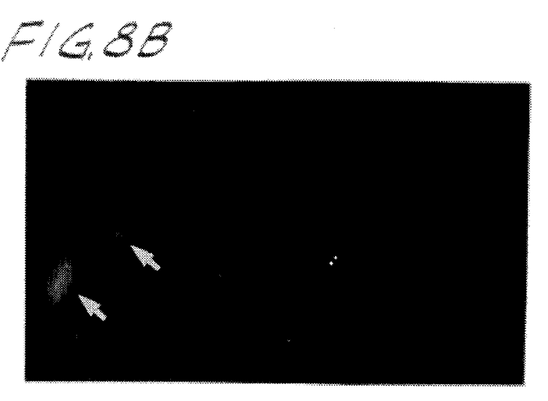
FIG. 8B: FITC—labelled attached BCG. Attached BCG are indicated by arrows.
Figure 8C:
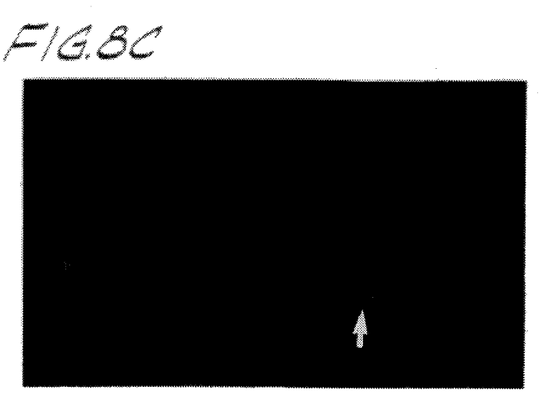
FIG. 8C: RITC labelled ingested BCG. The ingested BCG are indicated by the arrow. Attached BCG also are RITC labelled but are distinguished from ingested bacteria because they also are labelled by FITC (see FIG. 8B)
Figure 9A:
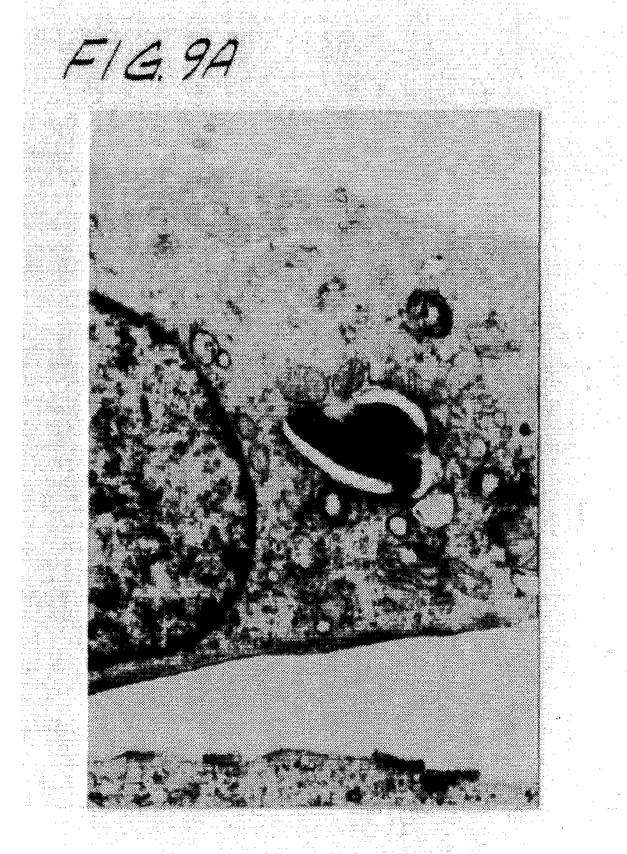
FIGS. 9A–9C are electron micrographs demonstrating BCG attachment and ingestion by T-24 cells. Magnification.
Figure 9B:
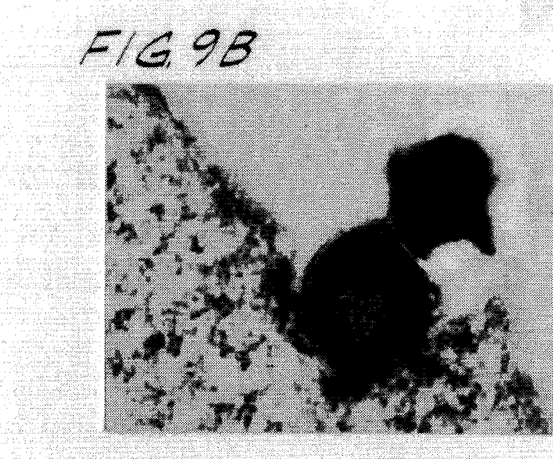
Figure 9C:
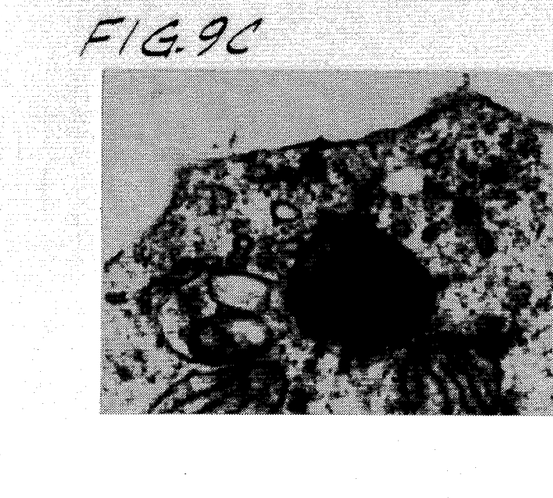

Attachment and ingestion was assessed by a modification of the double immunofluorescence assay described by Portnoy et al, (J. Exp. Med., 167: 1459–1471, 1988). After washing, 10% horse serum in PBS was added for 30 minutes to block non-specific antibody binding. Blocking was followed by the addition of a 1:100 dilution of polyclonal rabbit anti-BCG antibody for 30 minutes. After washing, 1:200 dilution of FITC conjugated goat anti-rabbit IgG was added for 30 minutes to stain extra-cellular BCG. After washing, methanol was added for 5 minutes to permeablize the T-24 cells. Subsequently, both extracellular and intracellular BCG were stained with RITC by adding anti-BCG antibody followed by 1:200 dilution of RITC conjugated goat anti-rabbit IgG as described for the FITC antibody. After washing, slides were mounted in a solution containing 50% glycerol and 0.1% p-phenylenediamine (Sigma Chemical Company, St. Louis, Mo.) in PBS. All staining procedures were carried out at room temperature, and all antibodies were diluted with 10% horse serum in PBS. A representative photograph demonstrating attached (stained with both FITC and RITC) and ingested (stained with RITC only) bacteria is provided in FIG. 8. An electron micrograph demonstrating both attachment and ingestion is shown in FIG. 9.

Assessment of BCG Attachment and Ingestion by T-24 Cells. In each experiment, a total of 100 cells were counted at a magnification of 1,000X. Attachment and ingestion rates are expressed as the percentage of cells that had extracellular and/or intracellular BCG among the total of 100 cells counted. If cells had both extracellular and intracellular BCG, they were scored as ingesting cells. All experiments were repeated three times on separate days. All data values are presented as mean ± SEM of three independent determinations. Statistical analysis was performed using the Student's paired t-test.

Inhibition Studies. BCG were incubated with anti-BCG antibody or T-24 cells were incubated with each anti-integrin receptor antibody at 37° C. in 5% $CO_2$ for 30 minutes after which BCG ingestion assay was performed. Antibodies were diluted with RPMI-1640. As a control, BCG of T-24 cells were incubated with medium only.

Anti-$\beta_1$ antibodies block attachment of T-24 cells to both FN and LN, while anti-$\alpha_5$ blocks attachment to only FN. In order to eliminate the influence of these antibodies on cellular attachment, FN-, VN-, or LN-coated plates were used as dictated by the experiment. T-24 cells attach and spread equally well on all three proteins (data not shown). Neither LN nor VN affected BCG attachment or ingestion to T-24 cells.

Electron Microscopy. The ingestion assay was performed as described above. Electron microscopy was performed as previously described (Becich et al. supra). Briefly, cells were fixed in 1% glutaraldehyde in Hanks Balanced Salt Solution and post-fixed in 1% $OsO_4$. The preparation was dehydrated through a series of acetone baths and embedded in Spurrs resin. Sections were cut and stained in 1% uranyl acetate and Reynold's lead.

Results

Figure 10A:
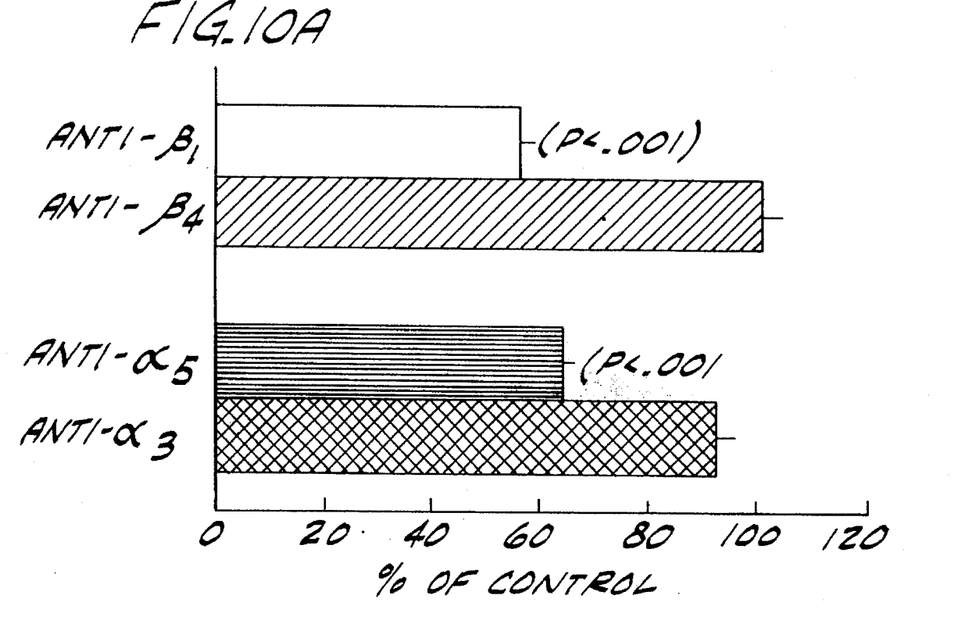
Figure 10B:
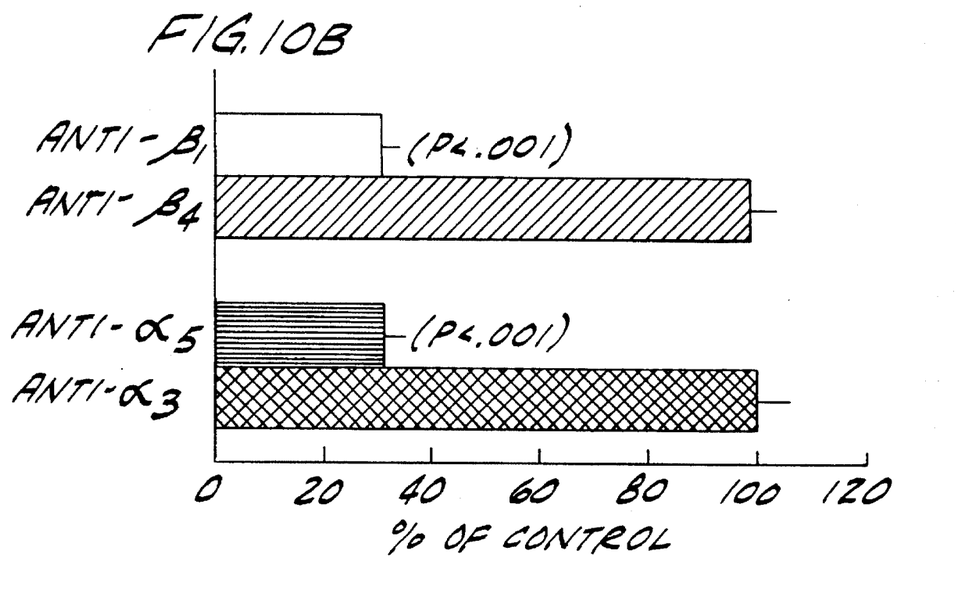

Effect of Anti-Integrin Receptor Antibodies on BCG Attachment and Ingestion by T-24 Cells. Previous studies demonstrated that transitional epithelial cells including the T-24 bladder tumor cell line ingested BCG (Becich et al. supra). Since previous reports demonstrated a role for integrin receptors in the ingestion of some bacteria by nonphagocytic cells, we evaluated the role of integrins in BCG attachment and ingestion. Flow cytometric analysis and immunoprecipitation studies of T-24 cells demonstrated the expression of $\alpha_2$, $\alpha_3$, $\alpha_5$, $\alpha_6$, $\alpha_v$, $\beta_1$, $\beta_3$ and $\beta_4$ integrin subunits and an absence of $\alpha_4$ (unpublished data). The role of these integrin components in BCG internalization was evaluated with monoclonal antibodies directed against specific integrin chains. The antibodies to $\beta_1$, $\alpha_3$ and $\alpha_5$ have been shown to block cellular attachment to extracellular matrix proteins, while the anti-$\beta_4$ is not a functionally inhibitory antibody (Hall et al., supra; Fradet et al., supra; Kennel et al., supra; Staquet et al., Exp. Cell Res. 187: 277–283, 1990). T-24 cells were pretreated with each antibody after which attachment and ingestion were quantitated. Inhibition of BCG attachment was observed for anti-$\beta_1$, and anti-$\alpha_5$, but not for anti-$\beta_4$ or anti-$\alpha_3$ antibodies (FIG. 10A). An even greater decrease in BCG ingestion was observed for anti-$\beta_1$, and anti-$\alpha_5$ (FIG. 10B). Table 2 (Experiment 1) contains raw data from a representative experiment demonstrating the effects of anti-integrins on attachment and ingestion. The inhibitory effect of these antibodies was dose dependent with a maximum inhibition at a 1:10 dilution of culture supernatant (data not shown).

TABLE 2

Effect of modulating agents on BCG, attachment and ingestion by T-24 cells. The Table contains representative experiments from each of four separate studies that are summarized in FIGS 10, 12 14, 17. The data are reported as the number of cells in each respective catagory/100 total cells.

| | No. Bacteria per coli | Experiment 1 (summarized in FIG 10) Anti-integrins[a] | | | | | Experiment 2 (summarized in FIG 12) Anti-ECM[b] | | | Experiment 3 (summarized in FIG 17) Anti-BCG FN Receptor[c] | | Experiment 4 (summarized in FIG 14) Opeonized BCG[d] | |
|---|---|---|---|---|---|---|---|---|---|---|---|---|---|
| | | Control | $\beta_4$ | $\beta_1$ | $\alpha_3$ | $\alpha_5\beta$ | Control | VN | FN | Control | Anti-p-55 | BSA | FN |
| Attached, unigested BCG | 1–2 | 17 | 15 | 8 | 22 | 14 | 16 | 15 | 2 | 17 | 10 | 14 | 5 |
| | 3–6 | 3 | 4 | 2 | 2 | 1 | 1 | 1 | 0 | 20 | 1 | 1 | 12 |
| | >6 | 0 | 2 | 1 | 0 | 0 | 3 | 2 | 0 | 7 | 0 | 0 | 10 |
| Ingested BCA | 1–2 | 10 | 10 | 4 | 8 | 4 | 7 | 6 | 1 | 9 | 1 | 5 | 2 |
| | 3–5 | 1 | 3 | 0 | 2 | 0 | 1 | 3 | 0 | 6 | 0 | 1 | 14 |
| | >6 | 1 | 0 | 0 | 2 | 0 | 2 | 3 | 0 | 8 | 0 | 1 | 3 |

Figure 11:
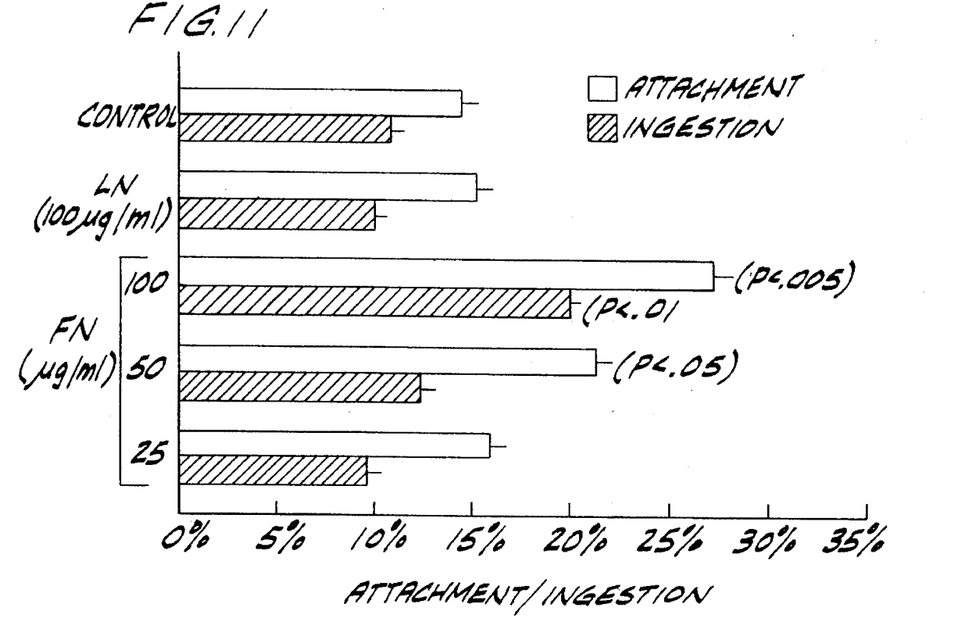
FIG. 11 is a graph showing the effects of FN on the attachment and ingestion of BCG by T-24 cells.
Figure 12:
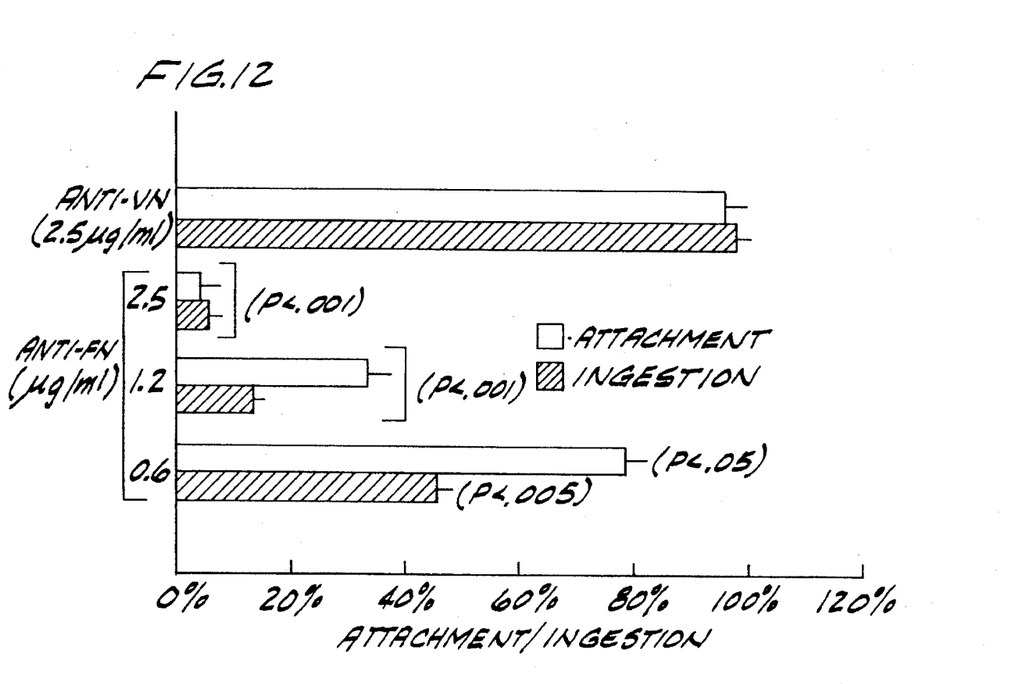
FIG. 12 is a graph showing the effect of polyclonal rabbit anti-FN on-BCG attachment and ingestion by T-24 cells.

[a]Antibody concentration, 1:10 dilution of culture supernatant
[b]ECM = extra cellular matrix protein; Antibody concentration, 2.5 μg/ml
[c]Antibody concentration, 1:5 dilution of culture supernatant; Assay performed on FN-coated surfaces
[d]BCG precoated with FN as described in Materials and Methods Role of Extracellular matrix Proteins in BCG Attachment and Ingestion by T-24 Cells, The integrin subunits $\alpha_5$ and $\beta_1$ together comprise the classical FN receptor, and T-24 have been demonstrated to attach to FN via this receptor (Coplen et al. supra). The antibody data suggest that the $\alpha_5\beta_1$ receptor is an important receptor for BCG attachment and ingestion. Since previous studies showed that BCG bind specifically to FN by a bacterial surface receptor (Ratliff et al. supra), we investigated whether FN acts as an opsonin in BCG attachment and internalization. Laminin (LN), which does not bind to BCG but mediates attachment and spreading of T-24 cells, also was tested (Aslanzadeh et al. supra). The addition of either soluble human plasma FN or murine LN had no effect on BCG attachment and ingestion (data not shown). This observation is consistent with our previous studies which demonstrated that physiologic salt concentrations inhibited the binding of soluble plasma FN to BCG. In contrast, precoating slides with FN augmented attachment and ingestion in a does dependent manner (FIG. 11). The highest concentration of FN (100 µg/well) increased BCG attachment by 91.8% (p<0.01) and ingestion by 82.3% (p<0.001). LN had no effect on either attachment or ingestion. T-24 attachment and spreading was indistinguishable on LN and FN coated surfaces. However, T-24 attachment and spreading on FN was maximal at a coating concentration of 10 µg/ml, which had no effect on BCG attachment. This suggested that the increased attachment and ingestion of BCG by T-24 on surfaces coated with high concentrations of FN resulted from BCG interaction with the adherent FN. The concentration of FN which induced maximal BCG attachment to FN-coated surfaces is consistent with this interpretation. These observations were equivalent for T-24 cells plated on FN for either 2 hours or overnight prior to the ingestion assay. All remaining experiments were performed using 2 hour adherence to surfaces coated with 100 µg/ml of LN or FN.

Figure 13A:
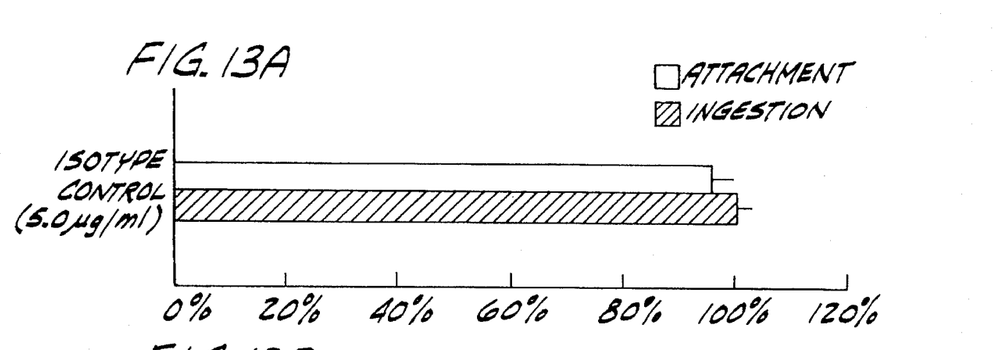
FIG. 13 is a graph showing the effect of monoclonal anti-FN, which inhibits cellular binding to the RGD cell binding site, on BCG attachment and ingestion by T-24 cells.
Figure 13B:
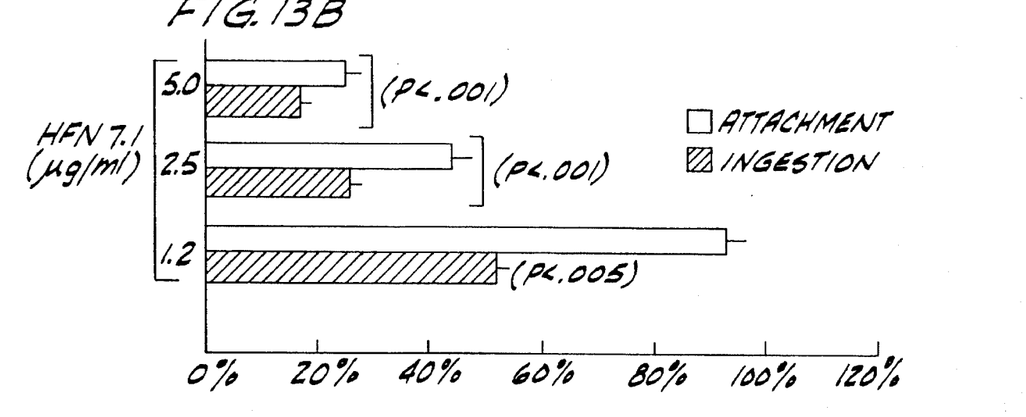
Figure 14:
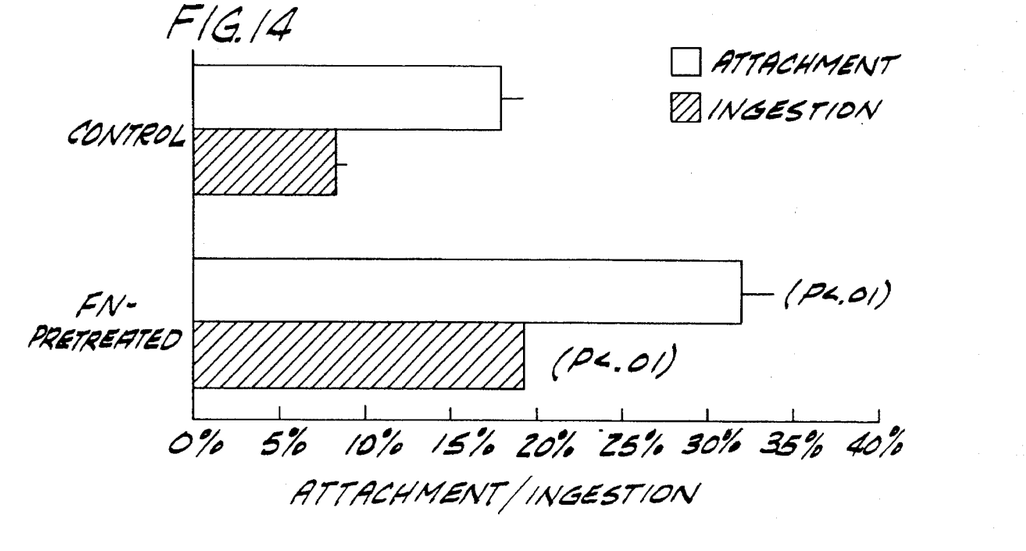
FIG. 14 is a graph showing the effect of FN pretreatment of BCG on attachment and ingestion by T-24 cells.

Further studies were performed to determine the effect of anti-FN antibody on attachment and ingestion by T-24 cells plated on LN coated surfaces. Purified rabbit polyclonal anti-FN inhibited attachment and ingestion by 91% and 88%, respectively (FIG. 12: Table 2, experiment 2). Inhibition by anti-FN was concentration dependent. No inhibition was observed using antibodies directed against vitronectin, which did not affect cell attachment or spreading on either FN or LN. Further studies were performed with a monoclonal antibody, HFN 7.1, which is known to block cell attachment to the RGD site on FN but not FN attachment to BCG (Bohnsack et al., supra). When T-24 cells were plated on LN, HFN 7.1 inhibited attachment and ingestion of BCG up to 60% and 70%, respectively (FIG. 13). Finally, pretreatment of BCG with FN under conditions which allow FN binding to BCG augmented attachment and ingestion by T-24 cells (FIG. 14; Table 1, experiment 4). These data show that FN can opsonize BCG, and that such opsonization enhances both BCG attachment and ingestion by T-24 cells on both a percentage basis and as a function of the number of bacteria associated with the cells.

Figure 15A:
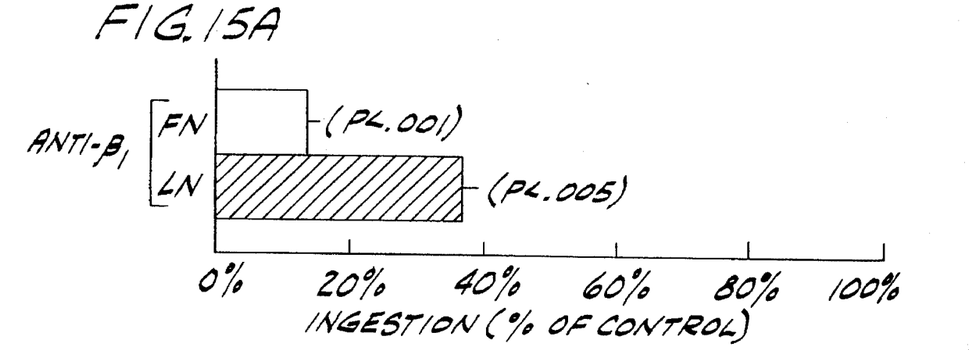
FIG. 15 is a graph showing the effect of anti-integrin antibodies on the ingestion of latex beads coated with either FN or LN. Antibody concentration, 1:10 dilution of cultured supernatant.
Figure 15B:
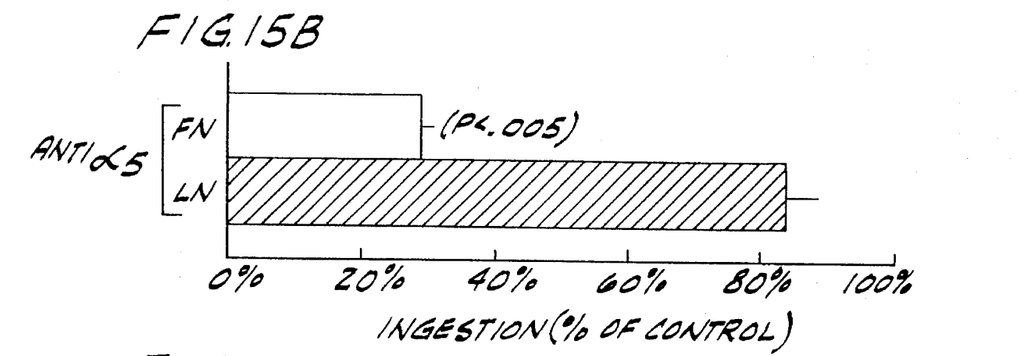

Since our data show that BCG attach to FN at a site distinct from the RGD cell binding site (data not shown), the potential for an opsonic role for FN was further investigated. Initially, polystyrene beads (3µ) were coated with either FN, LN or BSA, and attachment and ingestion of these beads were assessed using T-24 cells plated on VN. Both FN- and LN-coated beads attached and were ingested by T-24 cells, while BSA-coated beads were not ingested (data not shown). Further studies were performed to determine the effect of antibodies to the $\alpha_5$ and $\beta_1$ integrin subunits on ingestion. Both anti-$\alpha_5$ and $\beta_1$ inhibited the ingestion of FN-coated beads while only anti-$\beta_1$ inhibited the ingestion of LN-coated beads (FIG. 15).

Figure 16:
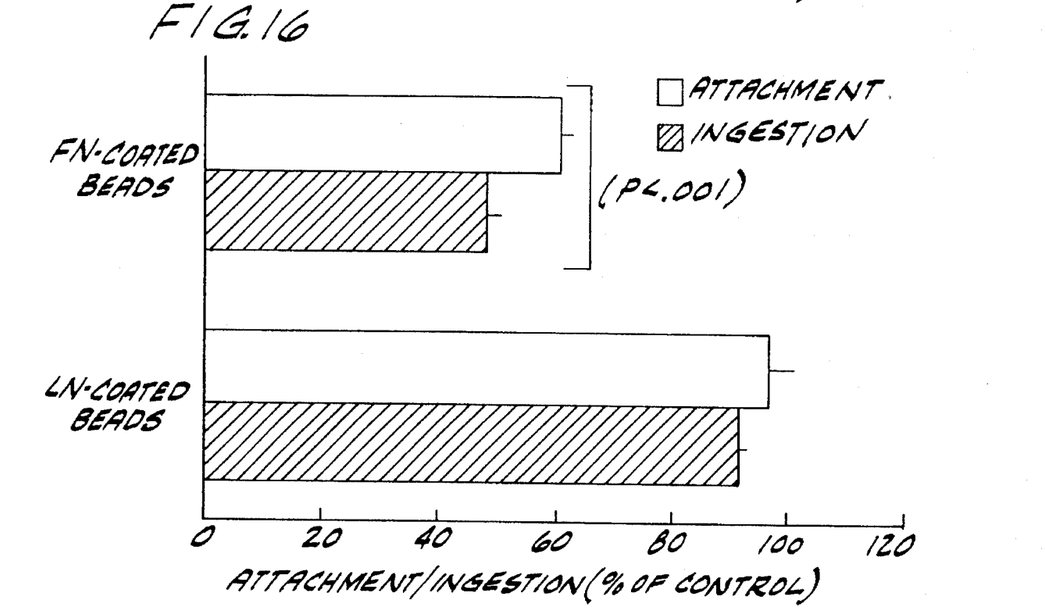
FIG. 16 is a graph showing the effect of FN-coated beads on the attachment and ingestion of BCG by T-24 cells.

Competition experiments were performed in which either LN- or FN-coated beads where co-incubated with BCG in the ingestion assay. FN-coated beads but not LN-coated beads inhibited BCG attachment and ingestion suggestion competition for the same T-24 receptor (FIG. 16).

Figure 17A:
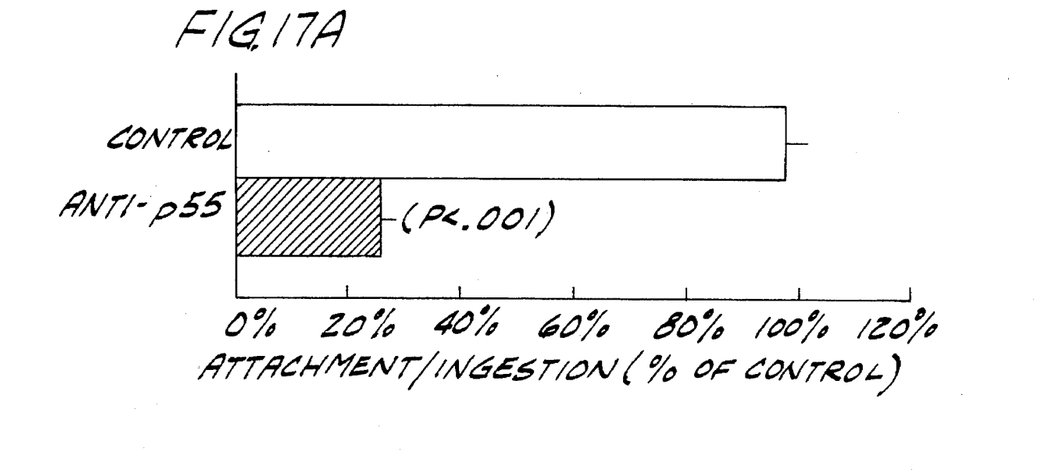
FIGS. 17A–17B are graphs showing the effect of monoclonal antibody to the BCG FN receptor (anti-p55) on BCG attachment FIG. 17A and ingestion FIG. 17B by T-24 cells.
Figure 17B:
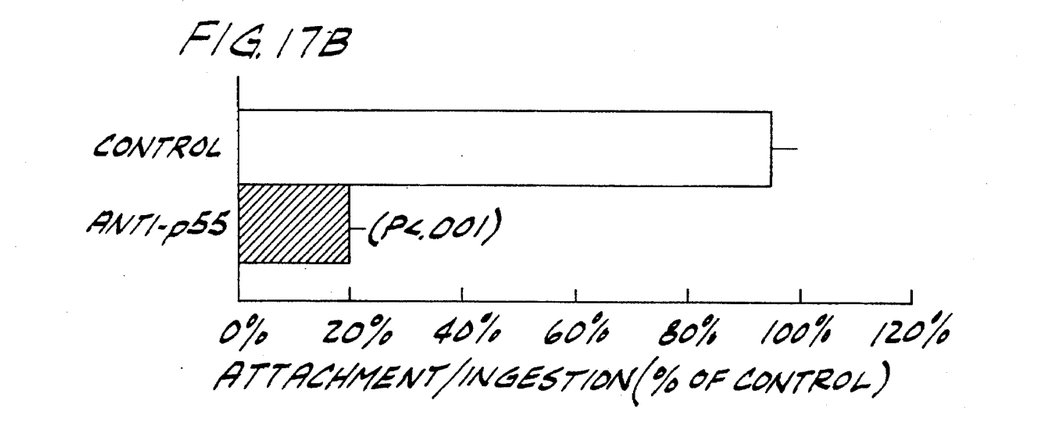

Effect on antibodies to BCG surface components on attachment and ingestion. To further explore the necessity for FN binding by BCG in attachment and ingestion by T-24, we evaluated the BCG surface structures required for recognition. Polyclonal anti-BCG completely inhibited both attachment and ingestion, demonstrating that a specific interaction was required (data not shown). Importantly, a mAb which recognizes the BCG 55 kD FN receptor (anti-p55) and prevents BCG attachment to FN (Ratliff, T. L., McCarthy R. J., and Brown, E. J. manuscript in preparation) also inhibited BCG attachment and ingestion (FIG. 17). These data demonstrate that this bacterial receptor is necessary for BCG attachment to T-24 cells, and are consistent with the hypothesis that FN mediates binding of BCG to this transitional epithelial cell line.

In view of the above, it will be seen that the several objects of the invention are achieved and other advantageous results attained.

As various changes could be made in the methods and products without departing from the scope of the invention, it is intended that all matter contained in the above description shall be interpreted as illustrative and not in a limiting sense.

What is claimed is:

1. A purified protein which functions as a mycobacterial receptor for fibronectin, said protein:

(a) binding directly to fibronectin, said binding being inactivated by trypsin;

(b) being essential for attachment of bacillus Calmette-Guerin to fibronectin;

(c) binding directly to fibronectin-coated surfaces;

(d) having a primary protein band at 55 kDa as determined by sodium dodecyl sulfate-polyacrylamide gel electrophoresis analysis on pooled fractions containing said purified protein;

(e) inhibiting fibronectin attachment to bacillus Calmette-Guerin in a dose-dependent manner;

(f) having a monoclonal antibody thereto which blocks the attachment of bacillus Calmette-Guerin to fibronectin-coated surfaces; and (g) having a polyclonal antibody that recognizes only the 55 kDa band in unfractionated bacterial extracts.

* * * * *